United States Patent
Shima

[19]

[11] Patent Number: 5,904,481
[45] Date of Patent: May 18, 1999

[54] SAMPLES OF ARTIFICIAL TEETH AND GUMS OF DISPLAY UNIT FOR DENTAL SURGEONS

[75] Inventor: Fumio Shima, Komatsushima, Japan

[73] Assignee: Shiken Corporation, Tokushima, Japan

[21] Appl. No.: 09/105,852

[22] Filed: Jun. 29, 1998

[30] Foreign Application Priority Data

Mar. 18, 1998 [JP] Japan .................................. 10-091001

[51] Int. Cl.⁶ ........................................................ A61L 19/10
[52] U.S. Cl. ............................................................. 433/26
[58] Field of Search ................................... 433/26, 203.1, 433/167, 171

[56] References Cited

U.S. PATENT DOCUMENTS

| | | | |
|---|---|---|---|
| 2,169,719 | 8/1939 | Bush | 433/167 |
| 2,262,641 | 11/1941 | Hayward | 433/26 |
| 2,383,027 | 8/1945 | Tryfus et al. | 433/26 |

FOREIGN PATENT DOCUMENTS 438458  5/1935  United Kingdom ................... 433/167

OTHER PUBLICATIONS

Myerson, The New Way, Journal of the American Dental Association, pp. A–14 and A–15, Aug. 8, 1940.

*Primary Examiner*—John J. Wilson
*Assistant Examiner*—Patrick A Hilsmier
*Attorney, Agent, or Firm*—Wenderoth, Lind & Ponack, L.L.P.

[57] ABSTRACT

A sample of artificial teeth and gums of a display unit for dental surgeons arranges plural artificial tooth samples forming the anterior teeth along the natural arch of the teeth. The artificial tooth samples are fixed and arranged on an artificial gum sample tinted with a determined color. The artificial gum sample has an inner face designed with a contact face curved to a form allowing it to be aligned close to the gum of the anterior teeth of the patient. A handle allowing the artificial gum samples to be aligned with the gum of the patient is fixed to the artificial tooth samples or to the artificial gum sample. With samples of the artificial tooth and gum, the artificial tooth samples and artificial gum samples are both aligned along the anterior teeth of the patient by holding the handles, allowing the patient to decide the color, shape and teeth arrangement of the artificial teeth and the artificial gum.

21 Claims, 3 Drawing Sheets

SAMPLES OF ARTIFICIAL TEETH AND GUMS OF DISPLAY UNIT FOR DENTAL SURGEONS

This application is based on No. 10-91001 filed in Japan on Mar. 18,1998, the content of which is incorporated hereinto by reference.

BACKGROUND OF THE INVENTION

The present invention relates to samples of artificial teeth and gums used by dentists to choose a gum of a display unit for dental surgeons, the color of the gum and the shape and the arrangement of the teeth by aligning the color samples of the artificial teeth and gum with the anterior teeth inside the mouth of the patient.

Color samples of artificial teeth do presently exist on the market, but there is no sample combining color, shape and arrangement (alignment) of artificial teeth and gums. Therefore, at present, considering the age, sex and particularities of the faces of patients, dentists have to decide the color, shape, and the like of artificial teeth and gums. Furthermore, patient preferences must be communicated orally or written by the dentist to the dental technician, therefore a drawback is that the artificial teeth and gums are usually not chosen according to the preferences of the patient. The reason is that the patient, the dentist and the dental technician have different images which do not perfectly match the display units for dentists.

To prevent these drawbacks, color samples have been developed to choose the color of the artificial teeth (The Japanese Non-examined Patent Publication No. 6-233784). As shown in the FIG. 1, a color sample mentioned in the above Publication is composed of plural artificial teeth 1 connected to a base plate 7 via rods 6.

With the artificial tooth sample 1 shown in FIG. 1, patients can choose the color of the artificial teeth according to their preferences. However, the artificial tooth sample 1 chosen by the patient cannot be color-matched by effective alignment with the patients' teeth. Furthermore, the color of the artificial teeth can be chosen, but there is the drawback that the arrangement of the artificial teeth and the color and the like of the gum cannot be chosen.

SUMMARY OF THE INVENTION

The present invention has been developed to solve the above drawbacks. The present invention helps to provide samples of artificial teeth and gums for a display unit for dental surgeons, allowing a patient to choose by setting the samples to the area of the anterior teeth of the patient. The ideal color, arrangement, shape and the like of the artificial teeth and gums which fit the patient best can then be chosen.

Samples of artificial teeth and gum of a display unit for dental surgeons of the present invention align along the natural arch of the teeth, with plural samples of artificial teeth forming the anterior teeth, and the artificial teeth being arranged and fixed on a gum sample of a determined color. The inner face of the gum sample has been shaped with a contact face curved to allow the sample to be brought close to the gum of the anterior teeth of the patient. Furthermore, a handle has been fixed to either the artificial tooth samples or to the artificial gum sample to allow the gum sample to be positioned along the gum of the patient. The samples of artificial teeth and gums of a display unit for dental surgeons are formed to allow the choice of color, shape and arrangement of the artificial teeth and gum while holding both the artificial tooth samples and the artificial gum sample by a handle in the vestibule of the mouth of the patient.

The samples of artificial teeth and gums of a display unit for dental surgeons of this structure allow the choice of color, shape, arrangement, and the like of artificial teeth and an artificial gum that is the most appropriate to the patient when aligned with the area of the anterior teeth of the patient. The reasons are that the samples of artificial teeth and artificial gum affix plural artificial tooth samples shaped like the anterior teeth on a gum sample colored with a fixed color, and both the artificial tooth samples and the artificial gum sample can be placed along the anterior teeth of the patient allowing the patient to choose the color, the shape and the arrangement of the artificial teeth and of the artificial gum. Placing the samples of artificial teeth and gum this way, which allows the choice of the artificial teeth and gum, along the anterior teeth of the patient, allows the patient himself to look, and to choose according to his preference. Therefore, image differences due to oral or written reports of the patient preferences are eliminated, and artificial teeth and gums which match the preferences of the patient can be effectively chosen.

Furthermore, the samples of artificial teeth and gum of a display unit for dental surgeons of this structure allow the choice of the artificial teeth and artificial gum fairly simply by aligning both the artificial teeth and the artificial gum along the anterior teeth by holding the handle which is fixed to either the artificial tooth samples or to the artificial gum sample, allowing the sample of gum to be brought along the gum of the patient. Then, because the samples of artificial teeth and artificial gum can be set holding the handle, the hand does not touch the interior of the mouth, and they can be used with extremely good hygiene.

The samples of artificial teeth and gum of the display unit for dental surgeons of the present invention can affix, according to preference, maxillary or mandibular artificial tooth samples to a separated maxillary or mandibular artificial gum sample. The maxillary and mandibular artificial gum samples, which are connected via handles, can be separated from each other.

The samples of artificial teeth and gum of a display unit for dental surgeons of this structure has the convenience of allowing use as an artificial teeth and gum sample for the upper jaw or for the lower jaw only. This is because the sample of artificial teeth and artificial gum fixes the maxillary and the mandibular artificial tooth samples to separate maxillary and mandibular artificial gum samples, and because the maxillary and mandibular gum samples are connected via handles allowing separation from each other. This way, the samples of artificial teeth and gum allow separate use of the upper jaw and of the lower jaw and allow the patient to choose under ideal conditions the most suitable artificial teeth and artificial gum by aligning the samples of artificial teeth and gum of the upper jaw only or of the lower jaw only with the anterior teeth of the patient, and by comparing the color or the balance with the adjacent natural teeth.

BRIEF DESCRIPTION OF THE DRAWINGS

The above and further features of the invention will be more fully apparent from the following detailed description of the accompanying drawings.

DETAILED DESCRIPTION OF THE INVENTION

Samples of artificial teeth and gums of the present invention are used to allow the patient himself to choose suitable artificial teeth and gums. Therefore, plural samples of artificial teeth and gums are used and provided with artificial tooth samples and artificial gum samples of different colors and shapes. With only one type of sample of artificial teeth and gums, the patient cannot choose the artificial tooth samples and the artificial gum samples which fit him. The plural samples of artificial teeth and gums have different shapes and colors of artificial tooth samples and artificial gum samples, or different arrangements of the artificial tooth samples. Aligning the artificial tooth samples and artificial gum samples with the area of his teeth, the patient can choose the color, the shape and the arrangement of the artificial tooth samples and the artificial gum samples. For this reason, plural samples of artificial teeth and artificial gums have different shapes and colors, and furthermore different teeth arrangements. For example, 36 sets of samples of artificial teeth and gums are used to realize a combination of 3 types of artificial tooth samples of different colors, 2 types of artificial gum samples of different colors, 2 types of artificial tooth samples of different sizes and 3 types of arrangements.

Figure 1:
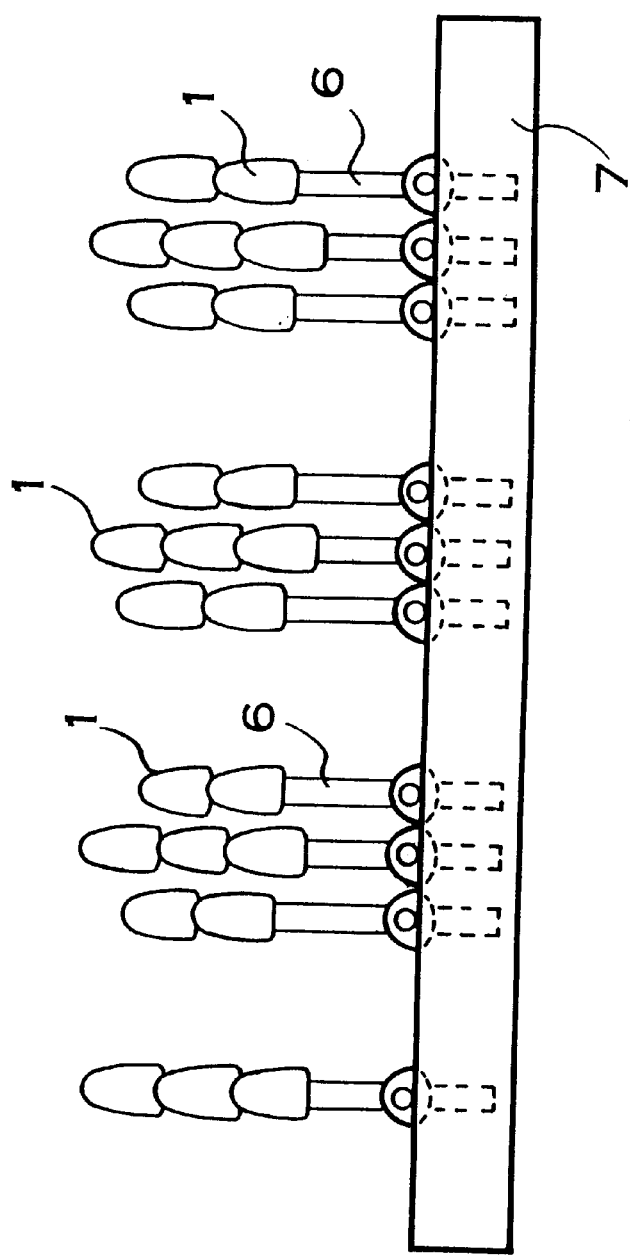
FIG. 1 is a front view showing an artificial tooth sample of the prior art.
Figure 2:
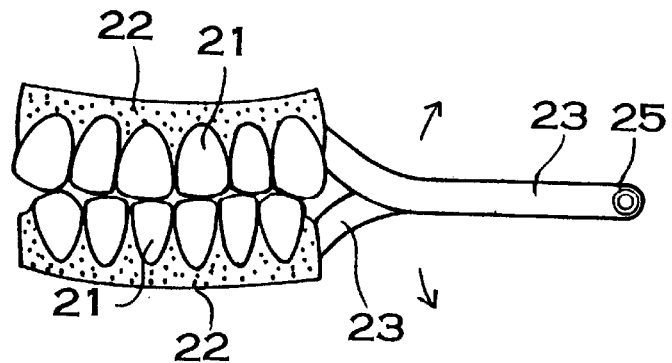
FIG. 2 is a front view showing an embodiment of a sample of artificial teeth and gums of a display unit for dental surgeons of the present invention.
Figure 3:
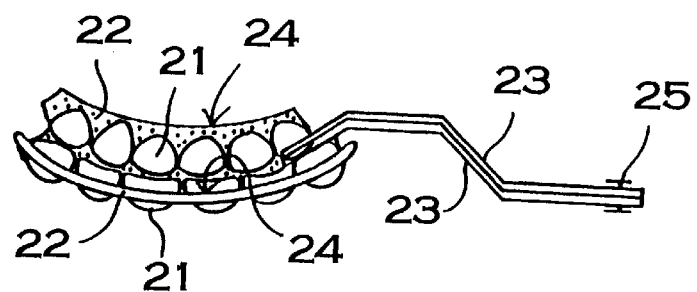
FIG. 3 is a plan view showing the sample of artificial teeth and gums shown in FIG. 2.

The sample of artificial teeth and gums of a display unit for dental surgeons shown in FIG. 2 and FIG. 3 arranges 6 artificial tooth samples on each upper jaw and on each lower jaw along the natural arch of the teeth. This sample of artificial teeth and gum shows one embodiment as an example, but plural samples of artificial teeth and gums have different forms and arrangements of the artificial tooth samples, and furthermore different colors and the like of the artificial tooth samples and artificial gum samples.

The sample of artificial teeth and gum in these Figs. is composed of a set of 6 artificial tooth samples for the anterior teeth, that is to say the 2 central incisors placed at the center, the 2 lateral incisors, one on each side, and the 2 cuspids, one on each side.

The sample of artificial tooth samples and gums in these Figs. arranges 6 artificial tooth samples 21 on each upper jaw and lower jaw, but the sample of artificial teeth and gums of the present invention does not necessarily need to fix 6 artificial teeth to the upper jaw and to the lower jaw on the gum samples 22. It is possible to mount, for example, 4 or even more than 8 artificial tooth samples on one artificial gum sample. The sample of artificial teeth and gum provided with 4 artificial tooth samples is composed of 2 central incisors at the center and 2 lateral incisors, one on both sides. The sample of artificial teeth and gum provided with more than 8 artificial tooth samples is composed of the molars added on both sides of the cuspids.

It is preferable to mount an even number of artificial tooth samples 21 on the artificial gum sample 22 of each sample of artificial teeth and gum. The reason is that the sample of artificial teeth and gum mounted with an even number of artificial tooth samples is symmetrical and can be arranged like natural human teeth along the anterior teeth of the patient. But an odd number of artificial tooth samples can also be set on the sample of artificial teeth and gum.

The artificial tooth samples 21 fixed on plural sets of samples of artificial teeth and gum are of different colors. But the artificial tooth samples 21 fixed on the same artificial gum sample 22 are all artificial tooth samples 21 of the same color. The colors of the artificial tooth samples 21 range from the light yellow to white. The greater the number of different colors used for the color sampling of the artificial tooth samples 21 is, the more suitable a choice of color of the artificial tooth samples can be made by the patient. But, when the number of color samples of the artificial tooth samples 21 is important, it becomes necessary to match the artificial tooth samples 21 of each color to the artificial gum sample 22 and to the size and arrangement of the artificial tooth samples 21, making a very important number of samples of artificial teeth and gum. Therefore, the number of artificial tooth samples 21 of different colors prepared for color sampling should be, for example, 3 to 5. Needless to say, it is possible to have fewer or greater sorts of colors.

Furthermore, the artificial tooth samples 21 are fixed on the artificial gum samples 22 to combine different shapes and sizes with different arrangements, thus making plural sets of samples of artificial teeth and gums.

The artificial gum sample 22 is colored with a color close to the natural human gum color. Furthermore, the artificial gum is designed on its surface with a pattern close to that of capillary vessels to make it look more like the natural human gum. Furthermore, the artificial tooth samples 21 and the artificial gum samples 22 are designed with a shape close to natural human teeth and gums. The teeth actually used as artificial teeth are used for the artificial tooth samples 21. The artificial gum, further, that is actually used for an artificial denture is used for the artificial gum sample 22.

The inner face of the artificial gum sample 22 to be introduced into the mouth of the patient is designed with a contact face 24 curved to a shape close to the shape of the gum of the natural anterior teeth. As shown in the FIG. 3, the contact face 24 is curved with a shape close to the arch of the maxillary teeth and to the arch of the mandibular teeth. As shown in the FIG. 4, the samples of artificial teeth and gums having maxillary and mandibular artificial teeth samples 21 have the maxillary contact face 24 protruding slightly more forward than the mandibular contact face 24 because the natural teeth are arranged in this fashion.

Figure 4:
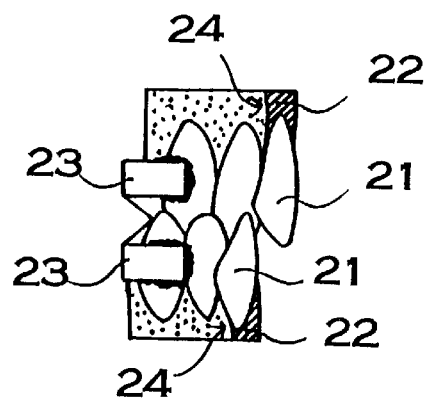
FIG. 4 is a partial cross-sectional view showing the sample of artificial teeth and gums shown in the FIG. 2.

A handle 23, as shown in FIG. 3 and in FIG. 4, is connected to the posterior face of the artificial gum sample 22. The handle 23 is bent forward as shown in FIG. 3 so as not to be hindered by the corners of the mouth when the artificial tooth samples 21 and the artificial gum samples 22 are introduced into the mouth of the patient and positioned on the anterior teeth.

In the samples of the artificial teeth and gums of FIG. 2, the rear extremities of the handles 23, which respectively connect their fore extremities to the upper jaw and to the lower jaw, are connected by a pin 25 allowing them to turn to separate the maxillary and the mandibular artificial gum samples 22. Having the pin 25 of the handle 23 located at the center and turning as shown by the arrows of FIG. 2, the sample of the artificial teeth and gum of this Fig. allows the separation of the maxillary and of the mandibular artificial gum samples 22. It is therefore possible to only introduce the upper jaw or only the lower jaw into the mouth of patient, using the sample as only a maxillary sample or only a mandibular sample of artificial teeth and gum.

Figure 5:
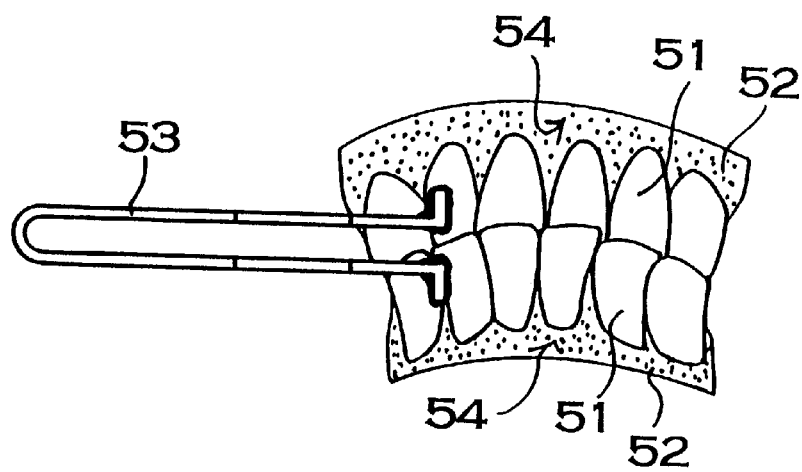
FIG. 5 is a rear view showing another embodiment of a sample of artificial teeth and gums of the present invention.

But, it is not necessary to make the handles connected to the maxillary and to the mandibular artificial gum samples turn. In the sample of artificial teeth and gum shown in the FIG. 5, the handles connecting the maxillary and the mandibular gum samples 52 are connected by their extremities. In the sample of artificial teeth and gum of this Fig., because there is no necessity to separate the maxillary and mandibular gum samples 52, it is possible to locally connect the maxillary and mandibular gum samples 52, and therefore the artificial tooth samples 51. The sample of artificial teeth and gum connecting the maxillary and mandibular gum samples 52 and the artificial tooth samples 51 is characterized by strength and by the fact that the maxillary and mandibular artificial tooth samples 51 do not slip out of place. In this Fig. the contact face is numbered 54.

Figure 6:
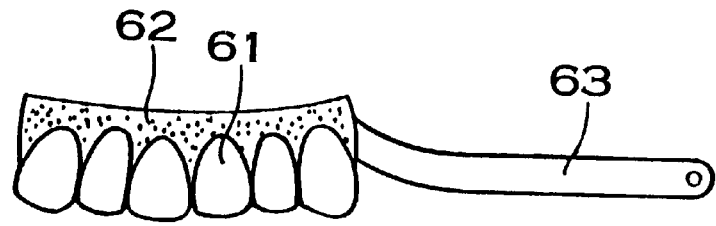
FIG. 6 is a front view showing another embodiment of a sample of artificial teeth and gum of the upper jaw.
Figure 7:
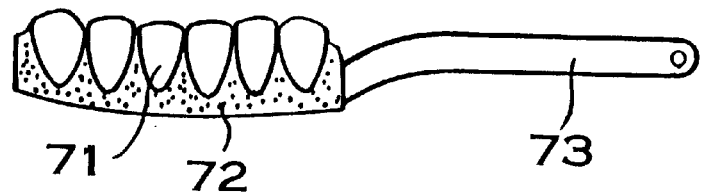
FIG. 7 is a front view showing another embodiment of a sample of artificial teeth and gum of the lower jaw.

Furthermore, the samples of artificial teeth and gum of the present invention can be used, as shown in FIG. 6, as samples of the maxillary artificial teeth and gum only, or as shown in FIG. 7, as samples of mandibular artificial teeth and gum only. According to these Figs., the artificial tooth samples are numbered 61 and 71, the artificial gum samples are numbered 62 and 72 and the handles are numbered 63 and 73.

The above described sample of artificial teeth and gums are manufactured according to the following process:

(1) Temporarily fix artificial tooth samples at a determined position of a mold which forms an artificial gum sample. The mold is composed of a forming chamber which holds the artificial tooth samples and of a forming chamber which forms the artificial gum sample. Furthermore, the mold is separated after having formed the artificial gum sample and has a structure allowing the extraction of the artificial gum sample having the artificial tooth samples inserted therein.

(2) While temporarily fixing the artificial tooth samples, fill a still un-hardened paste-like resin, which will form the artificial gum sample, into the forming chamber of the mold, and close the mold with clamps.

(3) Allow the un-hardened resin to harden through chemical reaction inside the forming chamber.

(4) Having allowed the resin which becomes the artificial gum sample to harden, open the forming chamber and extract the artificial gum sample having the artificial tooth samples inserted therein.

(5) Connect the extremity of the handle by use of an adhesive to the posterior face of the artificial gum sample. It is also possible to connect the handle, not to the posterior face of the artificial gum sample, but to the posterior face of the artificial tooth samples. Furthermore, the handle can be connected to the anterior faces of the artificial gum samples or the artificial tooth samples. But, samples of artificial teeth and gums connected with handles on their anterior faces are not suitable because, when aligned in the mouth of the patient, the handles are visible in front of the artificial tooth samples and in front of the artificial gum samples. Therefore, the handles should preferably be connected to the posterior face of the artificial tooth samples and the artificial gum samples.

As this invention may be embodied in several forms without departing from the spirit or essential characteristics thereof, the present embodiments are illustrative and not restrictive. Since the scope of the invention is defined by the appended claims rather than by the description preceding them, all changes that fall within metes and bounds of the claims, or equivalents of such metes and bounds thereof, are intended to be embraced by the claims.

What is claimed is:

1. Samples of artificial teeth and gums, comprising:

a plurality of artificial tooth samples representing anterior teeth;

an artificial gum sample having said plurality of artificial tooth samples fixed thereto along a natural tooth arch, said artificial gum sample being tinted with a predetermined color and having a curved inner contact face for close alignment with the gum of the anterior teeth of a patient; and a handle fixed to and extending from at least one of said plurality of artificial tooth samples and said artificial gum sample, said artificial gum sample and said plurality of artificial tooth samples having an anterior side, a posterior side, and an anterior direction from said posterior side toward said anterior side, and said handle being bent in said anterior direction;

whereby a patient can choose the color, shape and arrangement of artificial teeth and gum by holding said handle and aligning both said plurality of artificial tooth samples and said artificial gum sample along the anterior teeth of the patient.

2. The samples of claim 1, wherein said handle is fixed to said artificial gum sample.

3. The samples of claim 2, wherein said handle is fixed to a rear face of said artificial gum sample.

4. The samples of claim 3, wherein said handle bends forward between a free end thereof and a point at which said handle is fixed to the rear face of said artificial gum sample.

5. The samples of claim 3, wherein said handle is fixed to the rear face by an adhesive.

6. The samples of claim 1, wherein said handle is fixed to said plurality of artificial tooth samples.

7. The samples of claim 1, wherein said plurality of artificial tooth samples comprises six artificial tooth samples fixes to said artificial gum sample.

8. The samples of claim 1, wherein said plurality of artificial tooth samples comprises artificial tooth samples of the same color.

9. The samples of claim 1, wherein said artificial gum sample comprises a surface with a capillary vessel pattern thereon.

10. The samples of claim 1, wherein said plurality of artificial tooth samples are a first plurality of artificial tooth samples and said artificial gum sample is a first artificial gum sample, and further comprising a second plurality of artificial tooth samples and a second artificial gum sample, wherein:

said first plurality of artificial tooth samples are maxillary artificial tooth samples and said second plurality of artificial tooth samples are mandibular artificial tooth samples;

said first artificial gum samples is a maxillary artificial gum sample and said second artificial gum sample is a mandibular artificial gum sample;

said maxillary artificial tooth samples are fixed to said maxillary artificial gum sample and said mandibular artificial tooth samples are fixed to said mandibular artificial gum sample so as to form maxillary and mandibular samples; and said maxillary and mandibular samples are separable from each other.

11. The samples of claim 10, wherein said maxillary artificial gum sample has a contact surface and said mandibular artificial gum sample has a contact surface, said maxillary and mandibular artificial gum samples being positioned relative to each other such that said contact surface of said maxillary artificial gum sample is positioned forward of said contact surface of said mandibular artificial gum sample.

12. The samples of claim 10, wherein said handle is a first handle, and further comprising a second handle fixed to at least one of said second plurality of artificial tooth samples and said second artificial gum sample, and wherein said handles are connected to each other to connect said maxillary and mandibular samples.

13. The samples of claim 12, wherein said first and second handles are connected to each other so as to allow said maxillary and mandibular samples to be separable.

14. The samples of claim 12, wherein said first and second handles are connected to each other by a pin.

15. The samples of claim 10, wherein said maxillary and mandibular artificial gum samples are fixed with respect to each other.

16. The samples of claim 10, wherein said maxillary and mandibular artificial tooth samples are fixed with respect to each other.

17. The samples of claim 1, wherein said plurality of artificial tooth samples is a first plurality of artificial tooth samples, said artificial gum sample is a first artificial gum sample, and said handle is a first handle, and further comprising:

a second plurality of artificial tooth samples representing anterior teeth;

a second artificial gum sample having said second plurality of artificial tooth samples fixed thereto along a natural tooth arch, said second artificial gum sample being tinted and having a curved inner contact face for close alignment with the gum of the anterior teeth of a patient; and a second handle fixed to at least one of said second plurality of artificial tooth samples and said second artificial gum sample.

18. The samples of claim 17, wherein said first and second plurality of artificial tooth samples differ from each other in at least one condition selected from the group consisting of color, shape and arrangement of artificial teeth.

19. The samples of claim 17, wherein said first and second gum samples differ from each other in at least one condition selected from the group consisting of color, shape and arrangement of artificial teeth.

20. The samples of claim 1, wherein said artificial tooth samples are fixed to said artificial gum sample during manufacturing of said artificial gum sample.

21. The samples of claim 1, wherein said natural tooth arch forms a convexity on said anterior side and a concavity on said posterior side so as to have a convex side and a concave side, said handle being bent such that said handle is directed toward said convex side.

* * * * *